United States Patent
Serre et al.

(10) Patent No.: US 6,645,509 B1
(45) Date of Patent: Nov. 11, 2003

(54) POLYPEPTIDE EXPRESSED IN THE HORNY LAYER OF EPIDERMIS AND USE THEREOF

(75) Inventors: Guy Bruno Rene Serre, Toulouse (FR); Michel Simon, Belberaud (FR); Marina Weber-Vivat, Villefranche de Lauragais (FR)

(73) Assignee: Societe L'Oreal S.A., Paris (FR)

(*) Notice: Subject to any disclaimer, the term of this patent is extended or adjusted under 35 U.S.C. 154(b) by 0 days.

(21) Appl. No.: 09/381,656

(22) PCT Filed: Mar. 27, 1998

(86) PCT No.: PCT/FR98/00636

§ 371 (c)(1),
(2), (4) Date: Dec. 29, 1999

(87) PCT Pub. No.: WO98/44105

PCT Pub. Date: Oct. 8, 1998

(30) Foreign Application Priority Data

Mar. 28, 1997 (FR) .............................. 97 03899
Sep. 11, 1997 (FR) .............................. 97 11317

(51) Int. Cl.⁷ .............................................. A61K 6/00
(52) U.S. Cl. ........................ 424/401; 424/401; 424/409; 424/481; 424/59; 424/60; 424/94.63; 424/94.64; 424/94.65; 424/94.66; 424/94.67; 514/506; 514/529; 514/553; 514/844; 514/11; 514/943; 435/226; 435/252.3; 435/320.1; 435/69.1; 435/536; 435/23.2; 435/530; 435/350
(58) Field of Search ........................... 424/94.63, 94.64, 424/94.65, 194.66, 194.67, 401, 59, 481, 407, 409, 60; 514/506, 529, 553, 844, 846, 11, 943; 435/226, 320.1, 69.1; 536/23.2

(56) References Cited

U.S. PATENT DOCUMENTS 5,834,290 A * 11/1998 Egelrud et al. ............. 435/226
5,976,556 A * 11/1999 Norton et al. ............... 424/401

OTHER PUBLICATIONS

Zhou Y. et al, "Identification in the HLA class I region of a gene expressed late in keratinocyte differentiation" Proceedings of the National Academy of Sciences of USA, vol. 90, 1993, pp. 9470–9474, XP002049396, Washington D.C.
Lundstrom A. et al, "Evidence for a role of corneodesmosin, a protein which may serve to modify desmosomes during cornification, in stratum corneum cell cohesion and desquamation" Archives of Dermatological Research, 286 (7), 1994, 369–375, XP002075787.

Simon M. et al, "Characterization and purification of human corneodesmosin, an epidermal basic glycoprotein associated with corneocyte–specified modified desmosomes" Journal of Biological Chemistry, 272 (50) 1997, 31770–31776, XP002075788.
Serre G. et al, "Identification of late differentiation antigens of human cornified epithelia, expressed in re–organized desmosomes and bound to cross–linked envelope", Journal Invest. Dermatol., vol. 103, 1994, pp. 731–740, XP002075789.
F. Sakiyama et al., Chapter 85—*Lysyl endopeptidase, Handbook of Proteolytic Enzymes*, Alan J. Barrett et al. (eds.), 1998, pp. 261–263, Acdemic Press, London, England.
H. Stennicke et al., Chapter 79—*Glutamyl endopeptidase I, Handbook of Proteolytic Enzymes*, Alan J. Barrett et al. (eds.), 1998, pp. 243–246, Academic Press, London, England.
T. Yoshimoto et al., Chapter 125—*Prolyl oligopeptidase, Handbook of Proteolytic Enzymes*, Alan J. Barrett et al. (eds.), 1998, pp. 372–374, Academic Press, London, England.
S. Stone et al., Chapter 55—*Thrombin, Handbook of Proteolytic Enzymes*, Alan J. Barrett et al. (eds.), 1998, pp. 168–174, Academic Press, London, England.
J. Bieth, Chapter 15—*Leukocyte elastase, Handbook of Proteolytic Enzymes*, Allan J. Barrett et al. (eds.), 1998, pp. 54–60, Academic Press, London, England.

* cited by examiner

Primary Examiner—Christopher S. F. Low
Assistant Examiner—Hope A. Robinson
(74) Attorney, Agent, or Firm—Burns, Doane, Swecker & Mathis, L.L.P.

(57) ABSTRACT

The present invention relates to a cosmetic or pharmaceutical composition comprising, in a physiologically acceptable medium, a purified natural or synthetic epidermis-specific polypeptide which is involved in horny layer cell cohesion. The invention also relates to a cosmetic or pharmaceutical composition comprising a mixture of polypeptides derived from the proteolysis of the purified polypeptide of the present invention. The present invention further relates to a method for strengthening horny layer cell cohesion which comprises applying the cosmetic or pharmaceutical composition of the present invention to the skin. Finally, the present invention relates to a method for reducing horny layer cell cohesion, and thereby promoting exfoliation, wherein said method comprises applying to the skin a cosmetic or pharmaceutical composition comprising an effective amount of at least one protease active on the polypeptide of the present invention.

26 Claims, No Drawings

SEQUENCE LISTING

<160> NUMBER OF SEQ ID NOS: 2

<210> SEQ ID NO 1
<211> LENGTH: 529
<212> TYPE: PRT
<213> ORGANISM: Human

<400> SEQUENCE: 1

```
Met Gly Ser Ser Arg Ala Pro Trp Met Gly Arg Val Gly Gly His Gly
 1               5                  10                  15

Met Met Ala Leu Leu Leu Ala Gly Leu Leu Pro Gly Thr Leu Ala
                20                  25                  30

Lys Ser Ile Gly Thr Phe Ser Asp Pro Cys Lys Asp Pro Thr Arg Ile
             35                  40                  45

Thr Ser Pro Asn Asp Pro Cys Leu Thr Gly Lys Gly Asp Ser Ser Gly
         50                  55                  60

Phe Ser Tyr Ser Gly Ser Ser Ser Gly Ser Ser Ile Ser Ser
 65                  70                  75                  80

Ala Arg Ser Ser Gly Gly Ser Ser Gly Ser Ser Ser Gly Ser Ser
                 85                  90                  95

Ile Ala Gln Gly Gly Ser Ala Gly Ser Phe Lys Pro Gly Thr Gly Tyr
                100                 105                 110

Ser Gln Val Ser Tyr Ser Ser Gly Ser Gly Ser Ser Leu Gln Gly Ala
                115                 120                 125

Ser Gly Ser Ser Gln Leu Gly Ser Ser Ser His Ser Gly Ser Ser
        130                 135                 140

Gly Ser His Ser Gly Ser Ser Ser His Ser Ser Ser Ser Ser
145                 150                 155                 160

Phe Gln Phe Ser Ser Ser Phe Gln Val Gly Asn Gly Ser Ala Leu
                165                 170                 175

Pro Thr Asn Asp Asn Ser Tyr Arg Gly Ile Leu Asn Pro Ser Gln Pro
                180                 185                 190

Gly Gln Ser Ser Ser Ser Gln Thr Ser Gly Val Ser Ser Ser Gly
            195                 200                 205

Gln Ser Val Ser Ser Asn Gln Arg Pro Cys Ser Ser Asp Ile Pro Asp
        210                 215                 220

Ser Pro Cys Ser Gly Gly Pro Ile Val Ser His Ser Gly Pro Tyr Ile
225                 230                 235                 240

Pro Ser Ser His Ser Val Ser Gly Gly Gln Arg Pro Val Val Val Val
                245                 250                 255

Val Asp Gln His Gly Ser Gly Ala Pro Gly Val Val Gln Gly Pro Pro
            260                 265                 270

Cys Ser Asn Gly Gly Leu Pro Gly Lys Pro Cys Pro Ile Thr Ser
        275                 280                 285

Val Asp Lys Ser Tyr Gly Gly Tyr Glu Val Val Gly Gly Ser Ser Asp
    290                 295                 300

Ser Tyr Leu Val Pro Gly Met Thr Tyr Ser Lys Gly Lys Ile Tyr Pro
305                 310                 315                 320
```

```
Val Gly Tyr Phe Thr Lys Glu Asn Pro Val Lys Gly Ser Pro Gly Val
                325                 330                 335

Pro Ser Phe Ala Ala Gly Pro Pro Ile Ser Glu Gly Lys Tyr Phe Ser
            340                 345                 350

Ser Asn Pro Ile Ile Pro Ser Gln Ser Ala Ala Ser Ser Ala Ile Ala
        355                 360                 365

Phe Gln Pro Val Gly Thr Gly Val Gln Leu Cys Gly Gly Ser
    370                 375                 380

Thr Gly Ser Lys Gly Pro Cys Ser Pro Ser Ser Arg Val Pro Ser
385                 390                 395                 400

Ser Ser Ser Ile Ser Ser Ala Gly Ser Pro Tyr His Pro Cys Gly
                405                 410                 415

Ser Ala Ser Gln Ser Pro Cys Ser Pro Pro Gly Thr Gly Ser Phe Ser
            420                 425                 430

Ser Ser Ser Ser Ser Gln Ser Ser Gly Lys Ile Ile Leu Gln Pro Cys
        435                 440                 445

Gly Ser Lys Ser Ser Ser Ser Gly His Pro Cys Met Ser Val Ser Ser
    450                 455                 460

Leu Thr Leu Thr Gly Gly Pro Asp Gly Ser Pro His Pro Asp Pro Ser
465                 470                 475                 480

Ala Gly Ala Lys Pro Cys Gly Ser Ser Ala Gly Lys Ile Pro Cys
                485                 490                 495

Arg Ser Ile Arg Asp Ile Leu Ala Gln Val Lys Pro Leu Gly Pro Gln
            500                 505                 510

Leu Ala Asp Pro Glu Val Phe Leu Pro Gln Gly Glu Leu Leu Asp Ser
        515                 520                 525

Pro

<210> SEQ ID NO 2
<211> LENGTH: 1590
<212> TYPE: DNA
<213> ORGANISM: Human

<400> SEQUENCE: 2
atgggctcgt ctcgggcacc ctggatgggg cgtgtgggtg ggcacgggat gatggcactg      60
ctgctggctg gtctcctcct gccagggacc ttggctaaga gcattggcac cttctcagac     120
ccctgtaagg accccacgcg tatcacctcc cctaacgacc cctgcctcac tgggaagggt     180
gactccagcg gcttcagtag ctacagtggc tccagcagtt ctggcagctc catttccagt     240
gccagaagct ctggtggtgg ctccagtggt agctccagcg gatccagcat tgcccaggt     300 ggttctgcag gatcttttaa gccaggaacg gggtattccc aggtcagcta ctcctccgga     360
tctggctcta gtctacaagg tgcatccggt tcctcccagc tggggagcag cagctctcac     420
tcgggaagca gcggctctca ctcgggaagc agcagctctc attcgagcag cagcagcagc     480
tttcagttca gcagcagcag cttccaagta gggaatggct ctgctctgcc aaccaatgac     540
aactcttagc gcggaatact aaacccttcc cagcctggaa aaagctcttc ctcttcccaa     600
acctctgggg tatccagcag tggccaaagc gtcagctcca accagcgtcc ctgtagttcg     660
gacatccccg actctccctg cagtggaggg cccatcgtct cgcactctgg ccctacatc     720 cccagctccc actctgtgtc agggggtcag aggcctgtgg tggtggtggt ggaccagcac     780
ggttctggtg cccctggagt ggttcaaggt ccccctgta gcaatggtgg ccttccaggc     840
aagccctgtc ccccaatcac ctctgtagac aaatcctatg gtggctacga ggtggtgggt     900
```

-continued

| | | | | | |
|---|---|---|---|---|---|
| ggctcctctg | acagttatct | ggttccaggc | atgacctaca | gtaagggtaa | aatctatcct | 960 |
| gtgggctact | tcaccaaaga | gaaccctgtg | aaaggctctc | cagggqtccc | ttcctttgca | 1020 |
| gctgggcccc | ccatctctga | gggcaaatac | ttctccagca | accccatcat | ccccagccag | 1080 |
| tcggcagctt | cctcggccat | tgcgttccag | ccagtgggga | ctggtggggt | ccagctctgt | 1140 |
| ggaggcggct | ccacgggctc | caagggaccc | tgctctccct | ccagttctcg | agtccccagc | 1200 |
| agttctagca | tttccagcag | cgccggttca | ccctaccatc | cctgcggcag | tgcttcccag | 1260 |
| agcccctgct | ccccaccagg | caccggctcc | ttcagcagca | gctccagttc | ccaatcgagt | 1320 |
| ggcaaaatca | tccttcagcc | ttgtggcagc | aagtccagct | cttctggtca | cccttgcatg | 1380 |
| tctgtctcct | ccttgacact | gactgggggc | cccgatggct | ctccccatcc | tgatccctcc | 1440 |
| gctggtgcca | agccctgtgg | ctccagcagt | gctggaaaga | tccoctgccg | ctccatccgg | 1500 |
| gatatcctag | cccaagtgaa | gcctctgggg | ccccagctag | ctgaccctga | agttttccta | 1560 |
| ccccaaggag | agttactcga | cagtccataa | | | | 1590 |

POLYPEPTIDE EXPRESSED IN THE HORNY LAYER OF EPIDERMIS AND USE THEREOF

The subject of the invention is a cosmetic or pharmaceutical composition comprising, in a physiologically acceptable medium, at least one purified natural or synthetic polypeptide, specific to the epidermis, having a role in intercorneocyte cohesion. The subject of the invention is also a cosmetic or pharmaceutical composition comprising a mixture of polypeptides derived from the proteolysis of the purified polypeptide, a method of cosmetic treatment for strengthening intercorneocyte cohesion and a method of cosmetic treatment for reducing intercorneocyte cohesion, and therefore for promoting desquamation.

Human skin consists of two compartments, namely a deep compartment, the dermis, and a superficial compartment, the epidermis.

The dermis provides the epidermis with a solid support. It is also its feeder component. It consists mainly of fibroblasts and an extracellular matrix itself mainly composed of collagen, elastin and a substance called ground substance, these components being synthesized by the fibroblast. Leukocytes, mastocytes or tissue macrophages are also found therein. It also consists of blood vessels and of nerve fibers.

Natural human epidermis is composed mainly of three types of cells which are the keratinocytes, which are highly predominant, the melanocytes and the Langerhans' cells. Each of these cell types contributes, through its specific functions, to the essential role played by the skin in the organism.

The epidermis is conventionally divided into a basal layer of keratinocytes which constitutes the germinative layer of the epidermis, a so-called prickle cell layer consisting of several layers of polyhedral cells arranged on the germinative cells, a so-called granular layer consisting of flattened cells containing distinct cytoplasmic inclusions, the keratohyalin granules, and finally a top layer called horny layer (or stratum corneum), consisting of keratinocytes at the final stage of their differentiation, called corneocytes. These are anucleated, mummified cells which are derived from the keratinocytes.

The corneocytes are mainly composed of a fibrous matrix containing cytokeratins, surrounded by a very resistant structure 15 nm thick, called horny or hornified envelope. The stacking of these corneocytes constitutes the horny layer which is responsible for the barrier function of the epidermis. During the normal desquamation process, the most superficial corneocytes become detached from the surface of the epidermis.

Intercellular structures derived from the desmosomes, called corneosomes or corneodesmosomes, have been described in the horny layer. Recent studies have shown their key importance in intercorneocyte cohesion as well as in the desquamation process. In particular, a close correlation exists between cell dissociation and proteolysis of certain corneodesmosomal components such as desmoglein I.

Several serine proteases of the trypsin or chymotrypsin type appear to be involved in the proteolysis of the corneodesmosomes, in particular the chymotryptic enzyme of the horny layer (stratum corneum chymotryptic enzyme).

Numerous pathological conditions of the skin are characterized by the production of a thick horny layer and by an abnormal desquamation, that is to say by hyperkeratosis. The latter may occur on any anatomical skin area and in a wide variety of clinical contexts. Its physiopathological substratum and its cause are varied.

By way of example, there may be mentioned:

xerosis (or dryness of the skin), ichthyoses, psoriasis, certain benign or malignant tumour lesions, reactive hyperkeratoses.

Other pathological conditions are characterized by transdifferentiation or metaplasia, at the level of the mucosae, Malpighian or otherwise, but normally nonhornified, which become hornified, that is to say which become covered with an abnormal epithelium, producing a horny layer at its surface. Although the genital mucosae and those of the upper aerodigestive tracts are most often involved, these metaplasias may be seated in various anatomical areas.

By way of examples, there may be mentioned leukokeratosis of the uterine neck during prolapsus, buccal leukokeratoses, keratotic benign tumour lesions of the Malpighian mucosae By contrast, some pathological manifestations cause thinning of the epidermis and in particular of the horny layer, resulting in excessive fragility of the skin covering. It may be seated in various anatomical areas, its cause is variable and it may be constitutional or acquired.

By way of examples, there may be mentioned:

trophic skin disorders of the lower limbs in patients carrying vascular pathological conditions: varicose veins, arteriopathies (diabetes, arteriosclerosis and the like), trophic skin disorders in the context of an algodystrophic syndrome, trophic disorders following abnormal cicatrization.

The purification and knowledge of the polypeptides involved in intercorneocyte cohesion is one of the routes which could allow the production of products for combating the effects of an excess or a deficiency of polypeptides of this type, in particular at the surface of the skin.

One of the objects of the invention is to provide a composition comprising a polypeptide involved in intercorneocyte cohesion in purified form.

After long and laborious studies because of its low representation among the proteins of the epidermis, and its high instability and its high sensitivity to proteases, the applicant has identified, isolated and purified by biochemical techniques, from a human epidermis, a polypeptide specific to the hornified epithelia. This polypeptide, which will also be called elsewhere in the text "corneodesmosine" is expressed in the horny layer of the epidermis and is involved in intercorneocyte cohesion. The applicant has determined the primary amino acid sequence thereof.

The subject of the invention is therefore a cosmetic or pharmaceutical composition comprising, in a physiologically acceptable medium, at least one purified natural or synthetic polypeptide, the said polypeptide being characterized in that it corresponds to the following amino acid sequence SEQ ID NO: 1:

```
Met Gly Ser Ser Arg Ala Pro Trp Met Gly Arg Val Gly Gly His Gly
 1               5                  10                  15

Met Met Ala Leu Leu Ala Gly Leu Leu Pro Gly Thr Leu Ala
             20              25              30

Lys Ser Ile Gly Thr Phe Ser Asp Pro Cys Lys Asp Pro Thr Arg Ile
             35              40              45

Thr Ser Pro Asn Asp Pro Cys Leu Thr Gly Lys Gly Asp Ser Ser Gly
 50              55              60

Phe Ser Ser Tyr Ser Gly Ser Ser Ser Gly Ser Ser Ile Ser Ser
 65              70              75              80

Ala Arg Ser Ser Gly Gly Ser Ser Gly Ser Ser Gly Ser Ser
             85              90              95

Ile Ala Gln Gly Gly Ser Ala Gly Ser Phe Lys Pro Gly Thr Gly Tyr
             100             105             110

Ser Gln Val Ser Tyr Ser Ser Gly Ser Gly Ser Ser Leu Gln Gly Ala
             115             120             125

Ser Gly Ser Ser Gln Leu Gly Ser Ser Ser His Ser Gly Ser Ser
 130             135             140

Gly Ser His Ser Gly Ser Ser Ser His Ser Ser Ser Ser Ser
145             150             155             160

Phe Gln Phe Ser Ser Ser Phe Gln Val Gly Asn Gly Ser Ala Leu
             165             170             175

Pro Thr Asn Asp Asn Ser Tyr Arg Gly Ile Leu Asn Pro Ser Gln Pro
             180             185             190

Gly Gln Ser Ser Ser Ser Ser Gln Thr Ser Gly Val Ser Ser Ser Gly
             195             200             205

Gln Ser Val Ser Ser Asn Gln Arg Pro Cys Ser Ser Asp Ile Pro Asp
 210             215             220

Ser Pro Cys Ser Gly Gly Pro Ile Val Ser His Ser Gly Pro Tyr Ile
225             230             235             240

Pro Ser Ser His Ser Val Ser Gly Gly Gln Arg Pro Val Val Val
             245             250             255

Val Asp Gln His Gly Ser Gly Ala Pro Gly Val Val Gln Gly Pro Pro
             260             265             270

Cys Ser Asn Gly Gly Leu Pro Gly Lys Pro Cys Pro Pro Ile Thr Ser
             275             280             285

Val Asp Lys Ser Tyr Gly Gly Tyr Glu Val Val Gly Gly Ser Ser Asp
             290             295             300

Ser Tyr Leu Val Pro Gly Met Thr Tyr Ser Lys Gly Lys Ile Tyr Pro
305             310             315             320

Val Gly Tyr Phe Thr Lys Glu Asn Pro Val Lys Gly Ser Pro Gly Val
             325             330             335

Pro Ser Phe Ala Ala Gly Pro Pro Ile Ser Glu Gly Lys Tyr Phe Ser
             340             345             350

Ser Asn Pro Ile Ile Pro Ser Gln Ser Ala Ala Ser Ser Ala Ile Ala
             355             360             365

Phe Gln Pro Val Gly Thr Gly Gly Val Gln Leu Cys Gly Gly Ser
             370             375             380

Thr Gly Ser Lys Gly Pro Cys Ser Pro Ser Ser Ser Arg Val Pro Ser
385             390             395             400

Ser Ser Ser Ile Ser Ser Ser Ala Gly Ser Pro Tyr His Pro Cys Gly
             405             410             415

Ser Ala Ser Gln Ser Pro Cys Ser Pro Pro Gly Thr Gly Ser Phe Ser
             420             425             430
```

-continued

```
Ser Ser Ser Ser Ser Gln Ser Ser Gly Lys Ile Ile Leu Gln Pro Cys
        435             440             445

Gly Ser Lys Ser Ser Ser Ser Gly His Pro Cys Met Ser Val Ser Ser
        450             455             460

Leu Thr Leu Thr Gly Gly Pro Asp Gly Ser Pro His Pro Asp Pro Ser
465             470             475             480

Ala Gly Ala Lys Pro Cys Gly Ser Ser Ser Ala Gly Lys Ile Pro Cys
            485             490             495

Arg Ser Ile Arg Asp Ile Leu Ala Gln Val Lys Pro Leu Gly Pro Gln
            500             505             510

Leu Ala Asp Pro Glu Val Phe Leu Pro Gln Gly Glu Leu Leu Asp Ser
        515             520             525

Pro
```

The polypeptide of the invention may be of natural or synthetic origin. Synthetic is understood here to mean any polypeptide obtained chemically or by production in an organism after introducing into this organism the components necessary for this production.

The polypeptide of the invention may be derived from any possible origin, namely either animal, in particular mammalian and still more particularly human, origin or plant origin or from microorganisms (inter alia viruses, phages or bacteria) or from fungi, without prejudging the fact that it is present naturally or otherwise in the said organism of origin.

Preferably, the polypeptide of the invention is of natural origin, purified from mammalian tissues, particularly from mammalian skin.

Preferably, the polypeptide of the invention is purified from human skin and still more preferably from human epidermis.

As indicated above, intercorneocyte cohesion is apparently due, inter alia, to the existence, in the horny layer, of polypeptides specific to the structures involved in the intercorneocyte junction.

Accordingly, the polypeptide of the invention is specific to the horny layer and to the granular layer and, preferably, the polypeptide according to the invention is specific to the structures involved in the intercorneocyte junction, particularly of the corneodesmosomes.

It is known, in general, that the mature polypeptides which are found in cells are derived from the maturation of precursors which contain, in their sequence, the sequence of the mature polypeptide.

Accordingly, the invention also relates to a cosmetic or pharmaceutical composition comprising, in a physiologically acceptable medium, any polypeptide whose sequence partly consists of the sequence of the polypeptide of the invention.

It is also known that the polypeptides may undergo post-translational modifications such as the formation of disulphide bonds, specific proteolytic cleavages, the addition of carbohydrates (glycosylation), phosphorylation, in particular at the level of the serines and/or of the threonines and/or of the tyrosines, and/or combination with lipids.

The invention therefore relates to a cosmetic or pharmaceutical composition comprising, in a physiologically acceptable medium, at least one polypeptide of the invention which has undergone post-translational modifications or not.

The polypeptide of the invention may have undergone one or more post-translational modifications.

Preferably, the polypeptide according to the invention is glycosylated and/or phosphorylated.

It is known to classify polypeptides according to their isoelectric point. Preferably, the polypeptide of the invention is basic.

Of course the primary amino acid sequence as well as the various post-translational modifications undergone by the polypeptide are responsible for the fact that the said polypeptide may be characterized by its molecular weight, expressed in kilodaltons.

The polypeptide of the invention has an apparent molecular weight, determined by SDS-polyacrylamide gel electrophoresis (SDS-PAGE), of between 50 and 60 kilodaltons, preferably between 52 and 56 kilodaltons.

Most preferably, the polypeptide of the invention is a basic, phosphorylated, glycosylated polypeptide having an apparent molecular weight of between 50 and 60, preferably between 52 and 56 kilodaltons.

Thus preferably, the subject of the invention is a cosmetic or pharmaceutical composition comprising, in a physiologically acceptable medium, at least one polypeptide of the invention, the said polypeptide being phosphorylated, basic and glycosylated and having an apparent molecular weight of between 50 and 60 kilodaltons, preferably between 52 and 56 kilodaltons.

It is also known that the primary amino acid sequence of a polypeptide determines sites specifically recognized by proteases which, once the recognition of these sites has been achieved, will, with or without attachment to the said polypeptide, induce its cleavage by proteolysis.

Accordingly, the invention also relates to a cosmetic or pharmaceutical composition comprising, in a physiologically acceptable medium, at least one mixture of polypeptides derived from the proteolysis of the polypeptide of the invention.

As described above, some pathological conditions may be due to excessive desquamation which may be assumed to be due to a deficiency of polypeptides involved in intercorneocyte cohesion.

Some pathological manifestations cause thinning of the epidermis and, in particular, of the horny layer, resulting in excessive fragility of the skin covering, which may be seated in any anatomical skin area and may have various causes, constitutional or acquired.

Accordingly, the composition according to the invention is intended for treating the thinning of the epidermis, and in particular the horny layer, and/or for treating excessive fragility of the skin covering and/or for strengthening intercorneocyte cohesion and/or inducing the thickening of the horny layer.

Likewise, the composition according to the invention is intended for treating the thinning of the epidermis, and in particular of the horny layer and/or for treating excessive fragility of the skin covering and/or for strengthening intercorneocyte cohesion and/or inducing the thickening of the horny layer.

Likewise, the composition of the invention may be used for causing localized thickening of the horny layer at the level of the skin regions which have to be subjected to repeated microtraumas.

By way of example, there may be mentioned the preventive treatment of subepidermal blisters ("ampullae") in sportspeople.

The subject of the invention is also a method of cosmetic treatment for treating the thinning of the epidermis, and in particular of the horny layer, and/or for treating excessive fragility of the skin covering and/or for strengthening intercorneocyte cohesion and/or inducing the thickening of the horny layer, characterized in that a cosmetic composition according to the invention is applied to the skin of the subject to be treated.

The subject of the invention is also a method of cosmetic treatment for treating trophic skin disorders, for example of patients carrying vascular pathological conditions such as varicose veins or arteriopathies (diabetes, arteriosclerosis and the like), trophic skin disorders of patients carrying algodystrophic syndromes or those following cicatrization disorders.

Analysis of the primary amino acid sequence of the protein according to the invention shows that it has recognition and binding sites for known proteases or specific sites for cleavage by chemical agents. There may be mentioned, as example, the sites for Chymotrypsin, Cathepsin, proteinase K, Subtilisin, protease V8, Thermolysin, Thrombin, Trypsin, Papain, Pepsin, Proline-Endopeptidase, Endoproteinase GluC, Endoproteinase LysC, Endoproteinase AspN, Endoproteinase ArgC (Clostripain), Myxobacter AL117, Elastase, chymotryptic enzyme of the horny layer, cyanogen bromide, N-chlorosuccinimide or specific sites for acid hydrolysis (70% formic acid, 7 M Guanidine-HCl, 400° C., 24 h).

Intercorneocyte cohesion is apparently due to the existence, in the horny layer, of polypeptides soecific to the structures involved in the intercorneocyte junction such as, in particular, the polypeptide of the invention. It has been seen that certain hyperkeratotic pathological conditions could be linked to an excessive intercorneocyte cohesion, due in particular to the polypeptide of the invention.

Accordingly, the subject of the invention is a cosmetic or pharmaceutical composition comprising, in a physiologically acceptable medium, an effective quantity of at least one protease active on the polypeptide of the invention, chosen from Endoproteinase LysC, Endoproteinase GluC, Proline-Endopeptidase, Thrombin, Pepsin, Myxobacter AL117 and Elastase.

These proteases may be isolated from plants, animals, bacteria, viruses or fungi.

The polypeptide of the invention may be glycolysed. Accordingly, the composition as defined above may contain, in addition, a glycosidase which may be chosen from those isolated from plants, animals, fungi or microorganisms, in particular bacteria. There may be mentioned, by way of example, neuraminidases, mannosidases, galactosidases, glucosidases, N-acetylglucosaminidases and N-acetylgalactos aminidases.

As seen above, some pathological conditions are characterized by the production of a thickened epidermal horny layer and by abnormal desquamation, that is to say by hyperkeratosis which may occur in any anatomical skin area, in various clinical contexts and whose physiopathological substratum and cause may be varied.

The invention also relates to a cosmetic or pharmaceutical composition comprising a protease, as defined above, for treating, for example, hyperkeratosis, xerosis (or dryness of the skin), ichthyoses, psoriasis, certain benign or malignant hyperkeratotic tumour lesions, and reactive keratoses.

The invention also relates to a cosmetic or pharmaceutical composition comprising a protease, as defined above, for treating pathological conditions which are characterized by transdifferentiation or metaplasia, at the level of mucosae, Malpighian or otherwise, but normally nonhornified, which become hornified such as, for example, leukokeratosis of the uterine neck during prolapsus, buccal leukokeratoses, or benign or malignant hyperkeratotic tumour lesions of the Malpighian mucosae.

Another object of the invention is to provide a method of cosmetic treatment for combating excessive intercorneocyte cohesion and therefore for increasing desquamation and in particular the excesses due to the polypeptide of the invention, which method consists in applying to the skin a cosmetic composition comprising at least one protease having a specific recognition and/or binding and cleavage site within the primary amino acid sequence of the polypeptide of the invention.

It is known that a protein is synthesized in the cells from a template of deoxyribonucleic acids encoding the said protein. It is also known that the genetic code is degenerate. Accordingly, the amino acid sequence of the polypeptide of the invention may be derived from various natural or synthetic deoxyribonucleic acid sequences. Synthetic deoxyribonucleic acid sequence is understood here to mean any sequence obtained chemically or by genetic engineering.

The said deoxyribonucleic acid sequences may be derived from any possible origin, namely either animal, in particular mammalian and still more particularly human origin or plant origin or from microorganisms (inter alia viruses, phages, or bacteria) or from fungi, without prejudging the fact that they are present naturally or otherwise in the said organism of origin.

The applicant has isolated, purified and sequenced, using molecular biology techniques, in particular the screening of libraries for expression of complementary deoxyribonucleic acids prepared from human epidermis, a deoxyribonucleic acid fragment encoding the polypeptide of the invention.

The subject of the invention is also therefore a cosmetic or pharmaceutical composition comprising, in a physiologically acceptable medium, any deoxyribonucleic acid sequences, natural or synthetic, all or part of which encodes the primary amino acid sequence of the polypeptide of the invention.

During these studies, the applicant has been able to isolate and purify a deoxyribonucleic acid sequence encoding the primary amino acid sequence of the polypeptide of the invention from human skin.

Particularly, the subject of the invention is a cosmetic or pharmaceutical composition comprising, in a physiologically acceptable medium, an isolated deoxyribonucleic acid fragment comprising at least the following coding nucleotide sequence SEQ ID NO: 2:

```
   1 ATG GGC TCG TCT CGG GCA CCC TGG ATG GGG CGT GTG GGT GGG CAC
  46 GGG ATG ATG GCA CTG CTG CTG GCT GGT CTC CTC CTG CCA GGG ACC
  91 TTG GCT AAG AGC ATT GGC ACC TTC TCA GAC CCC TGT AAG GAC CCC
 136 ACG CGT ATC ACC TCC CCT AAC GAC CCC TGC CTC ACT GGG AAG GGT
 181 GAC TCC AGC GGC TTC AGT AGC TAC AGT GGC TCC AGC AGT TCT GGC
 226 AGC TCC ATT TCC AGT GCC AGA AGC TCT GGT GGT GGC TCC AGT GGT
 271 AGC TCC AGC GGA TCC AGC ATT GCC CAG GGT GGT TCT GCA GGA TCT
 316 TTT AAG CCA GGA ACG GGG TAT TCC CAG GTC AGC TAC TCC TCC GGA
 361 TCT GGC TCT AGT CTA CAA GGT GCA TCC GGT TCC TCC CAG CTG GGG
 406 AGC AGC AGC TCT CAC TCG GGA AGC AGC GGC TCT CAC TCG GGA AGC
 451 AGC AGC TCT CAT TCG AGC AGC AGC AGC AGC TTT CAG TTC AGC AGC
 496 AGC AGC TTC CAA GTA GGG AAT GGC TCT GCT CTG CCA ACC AAT GAC
 541 AAC TCT TAC CGC GGA ATA CTA AAC CCT TCC CAG CCT GGA CAA AGC
 586 TCT TCC TCT TCC CAA ACC TCT GGG GTA TCC AGC AGT GGC CAA AGC
 631 GTC AGC TCC AAC CAG CGT CCC TGT AGT TCG GAC ATC CCC GAC TCT
 676 CCC TGC AGT GGA GGG CCC ATC GTC TCG CAC TCT GGC CCC TAC ATC
 721 CCC AGC TCC CAC TCT GTG TCA GGG GGT CAG AGG CCT GTG GTG GTG
 766 GTG GTG GAC CAG CAC GGT TCT GGT GCC CCT GGA GTG GTT CAA GGT
 811 CCC CCC TGT AGC AAT GGT GGC CTT CCA GGC AAG CCC TGT CCC CCA
 856 ATC ACC TCT GTA GAC AAA TCC TAT GGT GGC TAC GAG GTG GTG GGT
 901 GGC TCC TCT GAC AGT TAT CTG GTT CCA GGC ATG ACC TAC AGT AAG
 946 GGT AAA ATC TAT CCT GTG GGC TAC TTC ACC AAA GAG AAC CCT GTG
 991 AAA GGC TCT CCA GGG GTC CCT TCC TTT GCA GCT GGG CCC CCC ATC
1036 TCT GAG GGC AAA TAC TTC TCC AGC AAC CCC ATC ATC CCC AGC CAG
1081 TCG GCA GCT TCC TCG GCC ATT GCG TTC AGC CAG TGG GGA CTG GTG
1126 GGG GTC CAG CTC TGT GGA GGC GGC TCC ACG GGC TCC AAG GGA CCC
1171 TGC TCT CCC TCC AGT TCT CGA GTC CCC AGC AGT TCT AGC ATT TCC
1216 AGC AGC GCC GGT TCA CCC TAC CAT CCC TGC GGC AGT GCT TCC CAG
1261 AGC CCC TGC TCC CCA CCA GGC ACC GGC TCC TTC AGC AGC AGC TCC
1306 AGT TCC CAA TCG AGT GGC AAA ATC ATC CTT CAG CCT TGT GGC AGC
1351 AAG TCC AGC TCT TCT GGT CAC CCT TGC ATG TCT GTC TCC TCC TTG
1396 ACA CTG ACT GGG GGC CCC GAT GGC TCT CCC CAT CCT GAT CCC TCC
1441 GCT GGT GCC AAG CCC TGT GGC TCC AGC AGT GCT GGA AAG ATC CCC
1486 TGC CGC TCC ATC CGG GAT ATC CTA GCC CAA GTG AAG CCT CTG GGG
1531 CCC CAG CTA GCT GAC CCT GAA GTT TTC CTA CCC CAA GGA GAG TTA
1576 CTC GAC AGT CCA TAA
```

The subject of the invention is also a cosmetic or pharmaceutical composition comprising, in a physiologically acceptable medium, a sense or antisense ribonucleic acid sequence corresponding to the said sequence SEQ ID NO: 2.

Its subject is also the use of the said deoxyribonucleic acid sequences for the production of the polypeptide of the invention or of a corresponding ribonucleic acid by any known technique such as for example synthesis in vitro, from reconstituted media, or synthesis by organisms.

The subject of the invention is also the use of the polypeptide of the invention or of its proteolysis fragments, and of any synthetic peptide deduced from its sequence, for preparing or purifying, optionally from the epidermis, any molecule, structural or functional, capable of binding specifically to the said purified polypeptide or to the said purified proteolysis fragments or to the said synthetic peptide. This molecule may in particular correspond to other structural proteins specific to the corneodesmosomes and various enzymes of the horny layer, of the "protease", "glycosidase" or "phosphatase" type.

The subject of the invention is also the use of the polypeptide of the invention or of its proteolytic fragments and of any synthetic peptide deduced from its sequence, for preparing specific monoclonal antibodies and antisera, intended in particular for purifying this protein and its fragments. By extension, the subject of the invention is also any use of the said sequence for producing recombinant antibodies or antibody fragments, regardless of the biological system used for producing the latter.

Whatever their nature, the compositions of the invention may be ingested, injected or applied to the skin (over any skin area of the body) or the mucosae (buccal, jugal, gingival, genital, conjunctival and the like).

Preferably, the compositions of the invention are applied to the skin or the mucosae.

Depending on the mode of administration, the compositions according to the invention may be provided in any of the galenical forms normally used.

For a topical application to the skin, the composition may take the form, in particular, of an aqueous or oily solution or of a dispersion of the lotion or serum type, of emulsions of liquid or semi-liquid consistency of the milk type, obtained by dispersion of a fatty phase in an aqueous phase (O/W) or conversely (W/O), or of suspensions or emulsions of soft consistency of the aqueous or anhydrous cream or gel type, or of microcapsules or microparticles, or of vesicular dispersions of the ionic and/or nonionic type or of foams or alternatively in the form of aerosol compositions also comprising a pressurized propellant. These compositions are prepared according to the customary methods.

For injection, the composition may be provided in the form of an aqueous or oily lotion or in the form of a serum. For the eyes, it may be provided in the form of drops, and for ingestion, it may be provided in the form of capsules, granules, syrups or tablets.

The quantities of the various constituents of the compositions according to the invention are those conventionally used in the fields considered.

These compositions constitute in particular cleansing, protective, treatment or care creams for the face, for the hands, for the feet, for the large anatomical folds or for the body, (for example day creams, night creams, make-up removing creams, foundation creams, antisun creams), fluid foundations, make-up removing milks, protective or care body milks, antisun milks, skincare lotions, gels or foams, such as cleansing lotions, artisun lotions, artificial tanning lotions, bath compositions, deodorant compositions containing a bactericidal agent, aftershave gels or lotions, depilatory creams, compositions against insect bites, antipain compositions or compositions for treating certain skin diseases such as eczema, rosacea, psoriasis, lichens and severe pruritus.

The compositions according to the invention may also consist of solid preparations constituting cleansing soaps or cakes.

The compositions may also be packaged in the form of an aerosol composition also containing a pressurized propellant.

The composition according to the invention may also be a composition for the care of the scalp, especially a shampoo, a hair setting lotion, a treatment lotion, a hair styling cream or gel, a dyeing (especially oxidation dyeing) composition optionally in the form of dyeing shampoos, restructuring lotions for the hair, a permanent-waving composition (especially a composition for the first stage of a permanent waving), a lotion or gel against hair loss, an antiparasitic shampoo and the like.

The composition may also be for dentibuccal use, for example a toothpaste. In this case, the composition may contain customary adjuvants and additives for compositions for buccal use and especially surfactants, thickening agents, humectants, polishing agents such as silica, various active ingredients such as fluorides, in particular sodium fluoride, and optionally sweetening agents such as sodium saccharinate.

When the composition is an emulsion, the proportion of fatty phase may range from 5% to 80% by weight, and preferably from 5% to 50% by weight relative to the total weight of the composition. The oils, waxes, emulsifiers and coemulsifiers used in the composition in the form of an emulsion are chosen from those conventionally used in the cosmetic field. The emulsifier and the coemulsifier are present in the composition in a proportion ranging from 0.3% to 30% by weight, and preferably from 0.5 to 20% by weight relative to the total weight of the composition. The emulsion may, in addition, contain lipid vesicles.

When the composition is an oily gel or a solution, the fatty phase may represent more than 90% of the total weight of the composition.

In a known manner, the cosmetic composition may also contain adjuvants common in the cosmetic field, such as hydrophilic or lipophilic gelling agents, hydrophilic or lipophilic additives, preservatives, antioxidants, solvents, perfumes, fillers, screening agents, odour absorbers and colouring materials. The quantities of these various adjuvants are those conventionally used in the cosmetic field, and for example from 0.01% to 10% of the total weight of the composition. These adjuvants, depending on their nature, may be introduced into the fatty phase, into the aqueous phase and/or into the lipid spherules.

As oils or waxes which can be used in the invention, there may be mentioned mineral oils (petroleum jelly), vegetable oils (liquid fraction of shea butter, sunflower oil), animal oils (perhydrosqualene), synthetic oils (Purcellin oil), silicone oils or waxes (cyclomethicone) and fluorinated oils (perfluoropolyethers), beeswaxes, carnauba or paraffin waxes. Fatty alcohols and fatty acids (stearic acid) may be added to these oils.

As emulsifiers which can be used in the invention, there may be mentioned for example glycerol stearate, polysorbate 60 and the PEG-6/PEG-32/Glycol Stearate mixture sold under the name Tefose$^R$ 63 by the company Gattefosse.

As solvents which can be used in the invention, there may be mentioned the lower alcohols, especially ethanol and isopropanol, and propylene glycol.

As hydrophilic gelling agents which can be used in the invention, there may be mentioned the carboxyvinyl polymers (carbomer), acrylic copolymers such as acrylate/alkylacrylate copolymers, polyacrylamides, polysaccharides such as hydroxypropylcellulose, natural gums and clays, and, as lipophilic gelling agents; there may be mentioned modified clays such as bentones, metal salts of fatty acids such as aluminium stearates and hydrophobic silica, ethylcellulose and polyethylene.

The composition may contain other hydrophilic active agents, such as proteins or protein hydrolysates, amino acids, polyols, urea, allantoin, sugars and sugar derivatives, water-soluble vitamins, plant extracts and hydroxy acids.

As lipophilic active agents, there may be used retinol (vitamin A) and its derivatives, tocopherol (vitamin E) and its derivatives, essential fatty acids, ceramides, essential oils, salicylic acid and its derivatives.

According to the invention, the composition may combine at least one extract of at least one Iridaceae with other active agents intended especially for the prevention and/or treatment of skin conditions. Among these active agents, there may be mentioned, by way of example:

- agents reducing skin differentiation and/or proliferation and/or pigmentation such as retinoic acid and its isomers, retinol and its esters, vitamin D and its derivatives, oestrogens such as oestradiol, kojic acid or hydroquinone;
- antibacterials such as clindamycin phosphate, erythromycin or antibiotics of the tetracycline class;
- antiparasitic agents, in particular metronidazole, crotamiton or pyrethroids;
- antifungal agents, in particular the compounds belonging to the imidazole class such as econazole, ketoconazole or miconazole or their salts, the polyene compounds, such as amphotericin B, the compounds of the allylamine family, such as terbinafine, or octopirox;
- antiviral agents such as acyclovir;
- steroidal anti-inflammatory agents such as hydrocortisone, betamethasone valerate or clobetasol propionate, or nonsteroidal anti-inflammatory agents such as, for example, ibuprofen and its salts, diclofenac and its salts, acetylsalicylic acid, acetaminophen or glycyrrhizic acid;
- anaesthetic agents such as lidocaine hydrochloride and its derivatives;
- antipruritic agents such as thenaldine, trimeprazine or cyproheptadine;
- keratolytic agents such as α- and β-hydroxycarboxylic or β-ketocarboxylic acids, their salts, amides or esters and more particularly hydroxy acids such as glycolic acid, lactic acid, salicylic acid, citric acid and, in general, fruit acids and 5-n-octanoylsalicylic acid;
- anti-free-radical agents, such as α-tocopherol or its esters, superoxide dismutases, certain metal chelators or ascorbic acid and its esters;
- antiseborrhoeic agents such as progesterone;
- antidandruff agents such as octopirox or zinc pyrithione;
- anti-acne agents such as retinoic acid or benzoyl peroxide.

Accordingly, according to a specific embodiment, the composition according to the invention also comprises at least one agent chosen from antibacterial, antiparasitic, antifungal, antiviral, anti-inflammatory, antipruritic, anaesthetic, keratolytic, anti-free-radical, antiseborrhoeic, antidandruff and anti-acne agents, and/or agents reducing skin differentiation and/or proliferation and/or pigmentation.

EXAMPLES

Monoclonal Antibodies

The murine monoclonal antibodies G36-19, F28–27 and B17–21 (IgG1) which are specific for the polypeptide of the invention, corneodesmosine, form part of a series of antibodies directed against epidermal differentiation antigens, produced after immunization of a mouse with a human plantar horny layer homogenate, and then characterized. The ascites of the monoclonal antibody MOPC-21 (IgG1) (Sigma Chemical Co., St Louis, Mo.) was used as negative control. The anti-phosphoserine antibody kit from Biomol Feinchenukalien GmbH (monoclonal antibody 1C8, 4A3, 4A9 and 4H4) and the monoclonal antibody PSR45 from Sigma were also used.

Isolation and Characterization of the Polypeptide Sequential Protein Extraction Starting with mammary skin (obtained from reductive mammaplasty), the epidermis was mechanically separated from the dermis after heat treatment of the skin for 5 minutes at 56° C. in a phosphate buffer, and then sequentially homogenized, at 4° C., in equal volumes of the following buffers (three times in each buffer: i) TE buffer: 40 mM Tris-HCl , pH 7.5; 10 mM ethylenediaminetetraacetate (EDTA); 0.25 mM phenylmethylsulphonyl fluoride and 2 µg/ml of each of the following inhibitors: aprotinin, pepstatin A and leupeptin; ii) TENP40 buffer: TE containing a detergent, Nonidet P-40 at 0.5%; iii) TEU buffers: TE containing various concentrations of urea (from 2 to 8 M). After each extraction, the homogenates were centrifuged for 15 minutes at 15,000 g and the supernatants collected. The first supernatant from each extraction was kept at –30° C. until the time of use. Finally, the pellet corresponding to the last extraction in the buffer containing 8 M urea was homogenized in TUDTT buffer: 35 mM Tris-HCl, pH 6.8; 8 M urea; 50 mM dithiothreitol; 5% glycerol; 0.25 mM phenylmethylsulphonyl fluoride and 2 µg/ml of each of the same inhibitors, incubated for 30 minutes at 95° C. and centrifuged as above. The protein concentrations were measured using the Pierce system (Coomassie Plus protein assay, Pierce Chemical Co., Rockford, Ill.).

Electrophoresis of the Proteins and Immunodetection

The proteins were separated by polyacrylamide gel electrophoresis in the presence of SDS (SDS-PAGE) in 7.5 or 10% acrylamide gels or by two-dimensional electrophoresis in the presence of urea, using the Pharmacia system (PhastSystem™; Pharmacia LKB). An isoelectric focusing (IEF) or a non-equilibrium pH gel electrophoresis (NEpHGE) was carried out in the first dimension, and then an SDS-PAGE was carried out in the second dimension with 12.5% polyacrylamide gels. For the two-dimensional electrophoreses, the proteins in the extracts in TENP40 buffer were precipitated with ethanol, collected by centrifugation and dissolved in 50 mM Tris-HCl, pH 7.4; 8 M urea and 0.5% β-mercaptoethanol. The marker proteins as well as the two-dimensional electrophoresis standards (2-D SDS-PAGE standards™) from Bio-Rad were used as molecular weight markers or as isoelectric point references.

After electrophoresis, the proteins were stained with Coomassie blue or with the aid of silver nitrate (silver stain plus kit Bio-Rad Lab.), or transferred to a reinforced nitrocellulose membrane (Schleicher & Schuell, Dassel, Germany). The membranes were then stained with Ponceau red or with Protogold (British BioCell International, Cardiff, UK) and immunodetected with monoclonal antibodies, as described above. The reactivities were revealed with the ECL™ kit from Amersham (ECL™ Western blotting kit, Amersham International, Aylesbury, UK), according to the manufacturer's protocol.

Results

The polypeptide of 52–56 kDa was detected in the extracts in TE and TEU buffers (starting from a urea concentration equal to 6 M), but not in the sequential extracts in TENP40 and TUDTT buffers. Furthermore, if the extract in TE buffer was centrifuged for 30 minutes at 100,000×g, the polypeptide was completely present in the supernatant. The monoclonal antibody G36-19 also recognized several polypeptides of lower apparent molecular weight, which were only partially extracted in the presence of urea (even at the concentration of 8 M), and were partially extracted in the presence of a reducing agent. Whether in TE buffer or in the presence of urea, no polypeptide was immunodetectable in the last of the three extracts produced. This indicates that the extraction was complete in each of the steps. The control experiments carried out in the absence of primary antibody or with the antibody MOPC-21 always proved to be negative. It is probable that the immunodetected forms of polypeptides of low molecular weight were not products of degradation generated during the extraction steps, since their proportion did not vary from one preparation to another and since the extractions were always carried out in the presence of protease inhibitors.

Human Corneodesmosine is a Component of the Horny Envelopes

In order to confirm, at the biochemical level, that the corneodesmosine is covalently linked to the horny envelopes, fragments, generated by proteolysis of envelopes highly purified from human plantar epidermis, were analysed with the monoclonal antibody G36-19.

Preparation and Analysis of the Horny Envelopes

Human horny envelopes were purified from the plantar horny layer and mammary epidermis, as described above. Briefly, the samples were extracted by repeated boiling, with vigorous stirring, in a solution containing 2% SDS (w/v) and dithiothreitol at the concentration of 25 mM, and than at 37° C. for 72 hours in a solution containing urea at the concentration of 8 M and dithiothreitol at the concentration of 25 mM. The envelopes extracted in urea were sedimented and then suspended in a solution containing 0.1% SDS, glycine at the concentration of 192 mM and Tris at the concentration of 125 mM. Finally, they were electrodialysed against this same buffer for 72 hours. The purified horny envelopes were then collected by centrifugation, washed with distilled water and counted. They were analysed morphologically, and then by indirect immunofluorescence, as described in the prior art. Digestion with protease V8 and immunodetection of the proteolysis products were carried out as described in the prior art.

Results

The envelopes were incubated for increasing periods with protease V8, and the fragments produced were separated by SDS-PAGE and immunodetected. The monoclonal antibody G36-19 strongly labelled a large number of bands having an apparent molecular weight greater than 50 kDa, some of which were located at the upper limit of the gel. This indicates that the corneodesmosine is incorporated inside the large-sized heteropolymeric structures resulting from the proteolysis of the envelope. Several bands stained with Protogold were not immunodetected, which confirms the specificity of the reaction. No band was clearly immunodetected with the monoclonal antibody G36-19 in the absence of proteolysis, which proves the existence of covalent bonds between corneodesmosine and other constituents of the horny envelopes.

None of the fragments produced by digestion of horny envelopes purified from mammary epidermis was immunodetected by the monoclonal antibody G36-19. In agreement with this result, these envelopes were a lot less labelled, and only at their periphery, when they were analysed with the monoclonal antibody G36-19 in indirect immunofluorescence.

Human Corneodesmosine of 52–56 kDa is a Basic Phosphoprotein

To determine the isoelectric point of corneodesmosine, human epidermis was extracted directly in a buffer containing a detergent (TENP40 buffer), and the proteins extracted were separated by two-dimensional electrophoresis (NEpHGE/SDS-PAGE) and immunodetected with the monoclonal antibody G36-19. The corneodesmosine of 52–56 kDa showed a basic isoelectric point greater than 8. This result was confirmed by immunodetection after IEF/SDS-PAGE separation. The protein immunodetected by the monoclonal antibody G36-19 was not visible after Coomassie blue staining, even when 100 µg of proteins in the extract in TENP40 buffer were loaded on the gel. This therefore suggests that the corneodesmbsine of 52–56 kDa is a quantitatively minor protein, representing less than 0.1% of the proteins extracted. Furthermore, the immunoreactive protein migrated in the form of several juxtaposed spots, suggesting the presence of post-translational modifications. To analyse the possible phosphorylation of human corneodesmosine, the latter was affinity-purified on a Sepharose matrix (HiTrap-NHS, Pharmacia) activated with N-hydroxysuccinimide groups and then coupled with the monoclonal antibody G36-19. Next, it was analysed by immunotransfer with antibodies specific for phosphoserine or for phosphotyrosine. One of the five anti-phosphoserine monoclonal antibodies used immunodetected corneodesmosine in a specific manner. In contrast, neither the monoclonal antibody PY20 nor an antiserum, directed against phosphotyrosine, recognized corneodesmosine.

Human Corneodesmosine of 52–56 kDa is a Glycoprotein

Affinodetection with Lectins

The corneodesmosine of 52–56 kDa was partially purified from an extract in TENP40 buffer by affinity chromatography. The bound corneodesmosine was eluted with 3% SDS, deposited on an electrophoresis gel and transferred onto nitrocellulose membranes. The membranes were incubated in a blocking buffer, and then with biotinylated lectins sold by Pierce Chemical Co., diluted to 1 µg/ml: agglutinin from Pisum sativum (PSA), from wheat germ (WGA), from Ricinus communis (RCA), from Dolichos bifluorus (DBA) and from Arachis hypogaea (PNA). After rinsing, the lectins were detected with streptavidin labelled with peroxidase (diluted 1/400,000), and the ECL™ kit from Amersham, as described above.

Deglycosylation Experiments

The extract in TENP40 buffer (10 µg) was kept boiling for 3 minutes in 20 µl of a sodium phosphate buffer at pH 7.2 containing 1% (w/v) of SDS. Nonidet P40 and EDTA were added in order to obtain a final concentration of, respectively, 1% and 20 mM. 2.4 units of N-glycosidase F (EC 3.2.2.18, Boehringer Mannheim) were added and the reaction mixture was incubated at 37° C. for 6 hours. The proteins (34 µg) of an extract in TENP40 buffer were also incubated with 5 mU of endo-α-N-acetylgalactosaminidase (EC 3.2.1.97) at 37° C. for 6 hours, in the presence or otherwise of N-glycosidase F or neuraminidase (EC 3.2.1.18), under the conditions described by the manufacturer (Oxford GlycoSystems Ltd., Abingdon, UK). The reactions were stopped by 2 minutes of boiling in sample buffer. The deglycosylation of fetuin, used as positive control, was tested by SDS-PAGE and with the biotinylated lectins.

The treated and untreated samples were separated by electrophoresis and analysed by immunodetection and affinodetection, as described above.

Chromatography on Concanavalin A-Sepharose

An extract in TENP40 buffer was directly injected, with a flow rate of 0.5 ml/minute, into a Concanavalin A Sepharose 4B column (ConA Sepharose, Sigma) which had been previously equilibrated with washing buffer: 20 mM Tris-HCl, pH 7.4, containing 0.2 M NaCl. After washing, with a flow rate of 1 ml/minute, with 15 ml of this buffer, the adsorbed proteins were eluted with a flow rate of 0.5 ml/minute with methyl-α-D-mannopyranoside (Sigma) diluted to 0.5 M in washing buffer. The proteins were then separated by SDS-PAGE and analysed as described above.
Results:

The proteins of an extract in TENP40 buffer, containing the 52–56 kDa corneodesmosine, were treated with various glycosidases and analysed in immunotransfer with two monoclonal antibodies directed against the polypeptide. The staining of the total proteins of the extract did not show apparent degradation during the incubation. The treatment with N-glycosidase F induced a reduction of about 5 kDa in the apparent molecular weight of the corneodesmosine. This result very strongly suggests an N-glycosylation. In contrast, the treatments with endo-α-N-acetyl-galactosaminidase and/or neuraminidase did not modify the migration of corneodesmosine. To confirm this result, human corneodesmosine was affinity-purified and analysed with the aid of biotinylated lectins. Wheat germ agglutinin (WGA) was strongly bound to the purified protein, unlike the other lectins tested which did not or very weakly recognized it. Furthermore, corneodesmosine bound to Concanavalin A coupled to a Sepharose matrix. It was possible to elute it with methyl α-D-mannopyranoside, a sugar which is specific for this lectin, at the concentration of 0.5 M, which proves the specificity of the binding.

Purification of Corneodesmosine:

After dermoepidermal cleavage, the epidermis was homogenized in TEA buffer: 40 mM Tris-HCl, pH 7.5; 10 mM EDTA; 10 μg/ml aprotinin and 4-(2-aminoethyl) benzenesulphonyl fluoride (Interchim, Paris, France) used at 0.8 mM. The homogenate was centrifuged for 15 minutes at 15,000 g. The supernatant was clarified by filtration on filters whose pore diameter is 0.45 μm (Puradisc™25 AS; Whatman, Clifton, N.J.), and injected with a flow rate of 0.3 ml/minute on an anion-exchange column (Hi Trap Q, Pharmacia LKB) which had been equilibrated in the washing buffer: 20 mM Tris-HCl, pH 7.5. The proteins not retained (that is to say about 5% of the total proteins of the extract) were directly injected at the same flow rate into an affinity column prepared as follows: about 2 mg of monoclonal antibody F28-27 were coupled to 1 ml of Sepharose 4B matrix activated by N-hydroxysuccinimide groups (HiTrap-NHS), as is recommended by the manufacturer Pharmacia LKB. The column was washed exhaustively with a flow rate of 1 ml/minute with the washing buffer in the presence and then in the absence of 1 M NaCl. The immunoadsorbed proteins were eluted with a flow rate of 0.3 ml/minute with 0.2 M glycine at pH 2.5; the pH of the eluted fractions was immediately neutralized with Tris base at a concentration of 2 M. The proteins of the different fractions were analysed in immunotransfer with the monoclonal antibody G36-19, or with the control monoclonal antibody MOPC-21. The fractions containing the proteins thus eluted were mixed, and then lyophilized. The proteins of the lyophilizate were analysed as described above, by one-or two-dimensional electrophoresis. The corneodesmosine was then cut out of the gel so as to be sequenced.

Results

The corneodesmosine of 52–56 kDa was purified by an anion-exchange chromatography followed by affinity chromatography. The entire corneodesmosine extracted is specifically bound to the affinity column, from which it was possible for it to be eluted in the presence of glycine. The staining with Protogold of the transferred proteins shows the high degree of purification obtained, since the corneodesmosine is highly predominant in these fractions. Similar results were obtained when the affinity chromatography was carried out on a matrix coupled with the monoclonal antibody F28-27 or with the monoclonal antibody G36-19. A two-dimensional gel analysis confirmed the basic isoelectric point of the purified corneodesmosine and showed that it is the only protein eluted having an apparent molecular weight of 52–56 kDa. The corneodesmosine thus purified was separated by electrophoresis and the gel band containing this protein was cut out and then the protein was sequenced.

Instability of the Purified Polypeptide

During its numerous trials to purify corneodesmosine, the applicant encountered two major problems: (1) the low proportion of this protein among the epidermal proteins and (2) its instability, possibly due to its high sensitivity to the action of proteases.

Different tests were used to try to stabilize the corneodesmosine: addition of zinc (inhibitor of the chymotryptic enzyme of the horny layer), reducing agents (β-mercaptoethanol or dithiothreitol), denaturing agents (SDS), glycerol, inhibitors specific for derise proteases (PMSF, aprotinin) or a cocktail of inhibitors of various proteases (aprotinin, leupeptin, pepstatin, benzamidine, phenanthroline, PMSF) or suppression of the freezing/thawing steps. Finally, the absence of freezing/thawing steps, the presence of 2% SDS or the presence of the cocktail of inhibitors, and preferably a combination of these conditions proved to be the most effective for stabilizing corneodesmosine.

Sequencing of the Purified Polypeptide

For the sequencing, the bands which correspond to corneodesmosine or to fragments of corneodesmosine (52–56 kDa, 45 kDa), identified on the electrophoresis gels were cut out. The proteins were then directly digested in the gel with the endopeptidase lys-C (EC 3.4.99.30) and the peptides generated were purified by HPLC using a DEAE-C18 column. The peptides thus selected were sequenced by the method of Edman degradation cycles on a Procise Sequencer apparatus from the company Applied Biosystems, according to the supplier's instructions.

Results

No sequencing from the $NH_2$-terminal end was possible, suggesting the protection of the protein at this end.

Internal sequencings made it possible to establish the sequence of two fragments, namely:

A: Lys Ser Tyr Gly Gly Tyr Glu Val Val Gly Gly Ser Ser Asp Ser Gly

B: Lys Ile Tyr Pro Val Gly Tyr Phe Thr Lys

This result confirms that obtained by the molecular biology techniques which allowed the deduction of the amino acid sequence of the polypeptide of the invention from the nucleotide sequence.

Construction of a Human Epidermis Expression Library

The cloning of the cDNA for human corneodesmosine could not be carried out using preexisting expression libraries. Indeed, the latter were produced either from mouse epidermis, or from human keratinocytes cultured in a monolayer, conditions which do not allow the expression of the genes characteristic of epidermal terminal differentiation. The applicant therefore constructed a human epidermal expression library.

Extraction of Poly(A)+ Ribonucleic Acids (RNA) From Human Epidermis

It was carried out using samples of mammary skin, surgical waste obtained after plastic surgery. The subcutaneous adipose tissue was dissected and then the skin pieces were cut up with the aid of a dermatome and incubated for 2 hours at 37° C., in a trypsin solution (solution A, Gibco BRL), epidermal face facing upwards. The dermo-epidermal cleavage was then carried out with tweezers. The epidermal sheets obtained were rinsed in phosphate buffer (PBS, pH 7.4). The extraction of the poly(A)+ RNAs was carried out according to the protocol proposed in the kit "mRNA purification kit" marketed by Dynal (Oslo), after homogenization of the sheets with the aid of a "Turax", directly in the buffer provided (lysis/binding buffer). The principle of this kit uses the affinity of the messenger RNA (mRNA) containing a poly(A) end for the magnetic beads coated with oligo(dT)$_{25}$. After 5 minutes of incubation at room temperature in the lysate, the beads were isolated with a magnet and subjected to 3 washes. The poly(A)+ RNAs eluted by incubating the beads at 65° C. for 2 minutes in a 2 mM EDTA solution, pH 8, were assayed using the "DNA Dip-Stick" colorimetric kit marketed by Invitrogen (San Diego, Calif.).

Construction of the Library

The library was constructed with the kit "ZAP Express cDNA Gigapack II Gold cloning kit" marketed by Stratagene (La Jolla, Calif.), following the protocol proposed by the supplier. The complementary DNAs (cDNA) were synthesized from 2 μg of poly(A)+ RNA, with the Moloney murine leukaemia virus reverse transcriptase (MMLV-RT), using oligo(dT)18 primers comprising a restriction site for the enzyme XhoI and in the presence of 5-methylcytidine triphosphate. The synthesis of the second strand was carried out by E. coli DNA polymerase I, and the ends of the cDNAs were made blunt with recombinant pfu polymerase. After addition of EcoRI adaptors (T4 DNA ligase), and phosphorylation of the 5' ends (T4 polynucleotide kinase), the cDNAs were subjected to digestion with the enzyme XhoI. The selection of the cDNAs having a size greater than 500 base pairs was carried out with a Sephacryl S-500 column. The ligation of the cDNAs with the two arms of the ZAP Express phage was carried out with T4 phage ligase. The encapsulation of the recombinant phage was carried out with the extracts "Gigapack II Gold Packaging Extract" provided by Stratagene. The strain XL-1 blue MRF' of E. coli was used for the titration and the spreading of the library.

Results

This library was prepared from 2 μg of mRNA, extracted from a fragment of human epidermis within the hours following its collection, by unidirectional cloning into the ZAP Express phage. It consists of about 2×10$^5$ independent clones.

Cloning of the Complementary Deoxyribonucleic Acid (CDNA) Encoding Corneodesmosine Immunological Screening The immunological screening, carried out without a prior amplification step, was performed on nitrocellulose membranes (Schleicher & Schuell, Dassel, Germany), incubated in an isopropyl-1-thio-β-D-galacto-pyranoside (IPTG, Stratagene) solution at 10 mM for 10 minutes, dried and incubated for 4 h at 37° C. on the spread library. The immunological screening procedure was carried out as described in the prior art with a cocktail of the three monoclonal antibodies G36-19, F28-27 and B17-21, used at the respective concentrations of 0.2, 0.2 and 2 μg/ml. The positive clones were isolated by conventional techniques and tested with each of the three monoclonal antibodies separately.

Sequencing

The ZAP Express phages corresponding to the purified clones were subjected to excision in vivo, with the aid of an ExAssist phage, as indicated by Stratagene. The plasmids obtained were amplified with the Qiagen kit (Hilden, Germany), and then sequenced at the ends of the inserts, with primers T3 and M13 (Stratagene), using a Perkin-Elmer kit (ABI PRISM Dye Terminator cycle sequencing kit, Perkin Elmer, Foster city, Calif.). Comparison of the sequences obtained with international databases was carried out with the Blast program.

Results

Given that the library was not amplified beforehand, the screening made it possible to isolate 5 independent clones. The human cDNA fragments contained in the clones were partially sequenced from the ends, which made it possible to show that they were all overlapping and therefore all encoded fragments of the same protein. The 5 clones were also tested with each of the three monoclonal antibodies separately. Three clones (1.1, 4.4 and 5.1) proved to be reactive with the three monoclonal antibodies, the clone 5.5 with two monoclonal antibodies (F28-27 and G36-19) and finally the clone 1.2 was recognized only by the monoclonal antibody F28-27. These results conclusively demonstrate that the three monoclonal antibodies recognize the same protein, thus confirming what had been strongly suggested by previous biochemical studies. These results also make it possible to order on the molecule the epitopes recognized by each of the monoclonal antibodies. Indeed, given that the clones were constructed by reverse transcription starting from the 3' end of the mRNAs, which corresponds to the COOH end of the protein, it is possible to conclude that the epitope recognized by F28-27 is closest to this end, followed by the epitope for G36-19 and finally that for B17-21. Enzymatic restriction analysis of the size of these different cDNA fragments confirmed that the 3 clones recognized by the 3 monoclonal antibodies have the longest sequences (from 2 to 1.5 kb), whereas that which only F28-27 recognizes is the shortest (1 kb), the last, recognized by 2 monoclonal antibodies, having an intermediate size of 1.3 kb.

Accordingly, all or part of the cDNA encoding human corneodesmosine was cloned, a protein characterized by the 3 monoclonal antibodies B17-21, G36-19 and F28-27 which recognize different epitopes, ordered on the protein in the order indicated, from the NH$_2$ end to the COOH end.

The partial sequences of each clone, compared with the sequences included in the international databanks, revealed a 99% identity with the sequence of the S gene, registered in the GenBank databank under the number L20815. This analysis also showed that among the 5 clones obtained, 4 correspond to the short form of the mRNA, only one, clone 5.1, corresponding to the long form. These forms are derived from an alternative choice of the polyadenylation site at the level of the noncoding 3' part of the primary transcript. This analysis made it possible to specify the location of the epitopes recognized by our 3 monoclonal antibodies, the epitope recognized by B17-21 is located in the part of the protein corresponding to nucleotides 594 to 762, G36-19 and F28-27 being respectively located in the 762-1044 and 1044-stop codon zone. Finally, the clone 1.1, which contains the longest coding sequence, starts at nucleotide 348.

Cloning of the Complete cDNA Encoding Corneodesmosine

The preceding analyses showed that the clones obtained did not cover the cDNA part extending from nucleotide 1 to nucleotide 347. The applicant therefore had to clone this missing part.

80 ng of poly(A)+ RNA extracted from human epidermis as described above were subjected to reverse transcription starting with random primers, using the kit "SuperScript" marketed by Gibco BRL. The amplification of the 5' end of the cDNA for corneodesmosine was carried out starting with ½₀ of the first strand synthesis reaction, with, upstream, an oligonucleotide corresponding to the sequence 2–20 (GenBank L20815) and also comprising an SpeI adapter, and, downstream, an oligonucleotide complementary to the sequence 1017–1035. The polymerase chain reaction (PCR) conditions were the following: 3 minutes at 94° C. followed by 35 cycles with 80 sec at 94° C., 80 sec at 57° C. and 2 minutes at 72° C. The single fragment obtained, purified after agarose-TBE gel electrophoresis, digested with SpeI and EcoNI (nucleotides 2 to 1003), was cloned into the plasmid pBK-CMV-1.1 (isolated by screening of the library) digested with the same enzymes, which made it possible to arrive at the plasmid ps11. The complete cDNA contained in the plasmid ps11 was sequenced at least 3 times up to nucleotide 1700. Comparison with the sequence previously published revealed four localized differences which were analysed at the genomic level.

Genomic Analysis of Corneodesmosine

Four localized differences were observed between the sequence of the complete cDNA isolated by the applicant and that of the S gene published in the prior art (Zhou Y. and Chaplin D. D., P. N. A. S. usa, Vol. 90, pp. 9470–9474, October 1993). These four localized differences were analysed by PCR, at the genomic level starting with ten control samples of DNA extracted from human blood according to conventional methods.

Analysis of the possible insertion of a guanine at position 1514 was carried out after PCR amplification of the genomic region between nucleotides 1446 and 1786 (GenBank, L20815), carried out under conventional conditions. The DNA fragment obtained for each sample was subjected to digestion with BsiMI on the one hand and NciI on the other. Electrophoresis on a 3% NuSieve GTG gel (FMC, Rockland, Me.) was carried out in TBE buffer.

The study of the sequence at position 66 was carried out according to the ASA (allele specific amplification) method. Two PCR reactions were carried out in parallel with, downstream, an oligonucleotide complementary to the sequence 572–91 and, upstream, an. oligonucleotide corresponding to the sequence 52–65 and ending at position 66 either with. A or with T. The PCR reactions were carried out with 0.5 µg of genomic DNA, 2.5 pmol of each oligonucleotide, and 0.5 U of Taq polymerase (Appligene). The amplification conditions are 94° C., 2 minutes and then 30 cycles with 50 seconds at 94° C., 1 minute at 56° C. and 2.5 minutes at 72° C.

Analysis of the bases at position 1118 and 1236 was carried out after amplification with a single oligonucleotide pair: sense oligonucleotide 908-27, antisense 1573-93. The PCR conditions are the same as above, with a polymerization time limited to 1 minute. The fragments were subjected to digestion with BsmI or Hin6 I for the respective study of positions 1118 and 1236 and then separated by electrophoresis on a 3% NuSieve gel.

Results

The insertion of a guanine at position 1514 causes a reading frame shift and moves the stop codon from position 1523 to position 1603. The protein produced by this sequence differs at the level of the last two amino acids (I and S) which are replaced by the sequence:

Asp Ile Leu Ala Gln Val Lys Pro Leu Gly Pro Gln Leu Ala Asp Pro Glu Val Phe

Leu Pro Gln Gly Glu Leu Leu Asp Ser Pro which corresponds to an addition of 27 amino acids relative to the published sequence. The 5. cDNAs previously, isolated all exhibited this insertion; the study was extended to other individuals. Ten control samples of human genomic DNA, obtained from ten individuals, were amplified in this region and analysed by enzymatic restriction. Indeed, the published sequence corresponds to the presence of a BsiMI restriction site at position 1510 which disappears in the sequence comprising an additional guanine, whereas an NciI site appears at 1512. The results are the same for the 10 individuals, namely that only the NciI site is present. This means that in these ten individuals, corneodesmosine is produced in a longer form than the published form of the S gene.

Three other localized differences, of the substitution type, were found between the clones and the published sequence. The analysis of the ten control genomic samples by PCR and enzymatic restriction or by ASA, showed that polymorphism of the gene is involved. The applicant has identified at position 66 a conservative mutation T/A (Leu-Met), at position 1118 a polymorphism A/G, corresponding to a silent mutation Ala-Ala and, finally, at 1236 a polymorphism T/G corresponding to a nonconservative mutation Ser-Ala.

Production of Recombinant Corneodesmosine

The complete cDNA encoding corneodesmosine was isolated, in the form of an Ecl136 I/NotI fragment of 2106 base pairs, from the plasmid pS11. The subcloning was carried out into the vector PCDNA amp (In Vitrogen) previously digested with EcoRV and NotI, leading to the plasmid p14-9.

The in vitro translation of corneodesmosine was carried out with the kit "TNT T7 Quick coupled transcription/translation system" marketed by Promega starting with the plasmid p14-9. This kit combines in one step the transcription with T7 phage RNA polymerase with translation with a rabbit reticulocyte lysate. These reactions were carried out with 0.6 µg of plasmid in a volume of 25 µl, according to the manufacturer's instructions.

Corneodesmosine was expressed in COS-7 cells after transfection with the plasmid p14-9. The cells were transfected according to the conventional DEAE-dextran protocol, supplemented by the addition of chloroquine and a DMSO shock, using 1 µg of plasmid/$3\times10^5$ cells. After 48 h of expression, the cells are washed twice with PBS, pH 7.4, and lysed in a 40 mM Tris-HCl buffer, pH 7.5, containing 10 mM EDTA and 0.5% NP40, and containing a cocktail of protease inhibitors (Pharmingen, Inc.). After SDS-PAGE separation and electrotransfer, the samples are immunodetected, as described above.

Results:

The new complete sequence of the protein predicts a molecular weight of 51.45 kDa, in the absence of any post-translational modification. The corneodesmosine synthesized in vitro, in the absence of microsomal membranes, migrates with an apparent molecular weight of about 60 kDa. This shows that this protein has an aberrant migration in SDS-PAGE gel. Comigration with the predominant epidermal form extracted in a low-ionic strength buffer demonstrates that the latter corresponds to a fairly extensively truncated form of the protein, all the more so since the applicant has shown that this epidermal form is glycosylated.

The transfection of COS-7 cells with the plasmid 14-9 reveals an immunoreactive protein which also migrates in the region of 60 kDa. The same results were obtained with the human neuroepithelioma line CHP 126, transfected by electroporation. All these results strongly suggest that in the epidermis, corneodesmosine undergoes, prematurely and during its maturation, a specific proteolysis.

What is claimed is:

1. A composition comprising, in a physiologically acceptable medium, one or more purified natural or synthetic polypeptide(s), wherein each of said polypeptide(s) comprises the amino acid sequence of SEQ ID NO: 1.

2. The composition according to claim 1, wherein said polypeptide(s) are purified from mammals.

3. The composition according to claim 1, wherein said polypeptide(s) are purified from mammalian skin.

4. The composition according to claim 1, wherein said polypeptide(s) are purified from human skin.

5. The composition according to claim 1, wherein said polypeptide(s) are purified from human epidermis.

6. The composition according to claim 1, wherein said polypeptide(s) are involved in intercorneocyte cohesion.

7. The composition according to claim 1, wherein each of said polypeptide(s) comprising amino acid sequence (SEQ ID NO: 1) has an apparent molecular weight of between 50 and 60 kilodaltons, as determined by SDS-PAGE.

8. The composition according to claim 1, wherein said polypeptide(s) are basic.

9. The composition according to claim 1, wherein said polypeptide(s) are glycosylated.

10. The composition according to claim 1, wherein said polypeptide(s) are phosphorylated.

11. The composition according to claim 1, wherein each of said polypeptide(s) is phosphorylated, basic and glycosylated and has an apparent molecular weight of between 50 and 60 kilodaltons, as determined by SDS-PAGE.

12. The composition according to claim 1, which comprises a mixture of polypeptides derived from the proteolysis of said polypeptide(s).

13. The composition according to claim 1 intended for treating the thinning of the epidermis.

14. The composition according to claim 1 for treating trophic skin disorders or trophic skin disorders following cicatrization disorders.

15. A method for treating the thinning of the epidermis, comprising administering to the skin of a subject in need of treatment an effective amount of a composition comprising, in a physiologically acceptable medium, one or more purified natural or synthetic polypeptide(s), wherein each of said polypeptide(s) comprise the amino acid sequence of SEQ ID NO: 1.

16. A method for treating trophic skin disorders or trophic skin disorders following cicatrization disorders comprising administering an effective amount of a composition comprising, in a physiologically acceptable medium, one or more purified natural or synthetic polypeptide(s), wherein each of said polypeptide(s) comprise the amino acid sequence of SEQ ID NO: 1.

17. A cosmetic or pharmaceutical composition comprising, in a physiologically acceptable medium, a purified natural or synthetic polypeptide comprising the amino acid sequence of SEQ ID NO: 1.

18. A composition comprising, in a physiologically acceptable medium, a nucleic acid molecule comprising the coding nucleotide sequence of SEQ ID NO: 2.

19. The composition according to claim 1, wherein said polypeptide(s) strengthen intercorneocyte cohesion.

20. The composition according to claim 1, wherein said polypeptide(s) are specific to the horny and granular layers.

21. The composition according to claim 1, wherein said polypeptide(s) are specific to the structures involved in the intercorneocyte junction.

22. The composition according to claim 1 intended for treating excessive fragility of the skin.

23. The composition according to claim 1 intended for strengthening intercorneocyte cohesion.

24. The composition according to claim 1 intended for inducing the thickening of the horny layer.

25. A method for strengthening intercorneocyte cohesion, comprising administering to the skin of a subject in need of intercorneocyte cohesion strengthening an effective amount of a composition comprising, in a physiologically acceptable medium, one or more purified natural or synthetic polypeptide(s), wherein each of said polypeptide(s) comprise the amino acid sequence of SEQ ID NO: 1.

26. A method of promoting desquamation to the skin of a subject in need of desquamation promotion, comprising administering an effective amount of the composition in a physiologically acceptable medium, one or more purified natural or synthetic polypeptide(s), wherein each of said polypeptide(s) comprise the amino acid sequence of SEQ ID NO:1.

* * * * *